United States Patent [19]

Benini

[11] 4,090,794
[45] May 23, 1978

[54] OPTICAL CIGARETTE END INSPECTION DEVICE

[76] Inventor: Fernando Benini, Via Predosa 21, Zola, Predosa, Bologna, Italy

[21] Appl. No.: 691,919

[22] Filed: Jun. 1, 1976

[51] Int. Cl.$^2$ .......................................... G01N 21/48
[52] U.S. Cl. .................................. 356/209; 250/202; 250/223 R; 356/237
[58] Field of Search ....................... 356/209, 212, 237; 250/223 R, 202

[56] References Cited

U.S. PATENT DOCUMENTS

| 2,840,722 | 6/1958 | Frommer | 250/202 |
| 3,980,567 | 9/1976 | Benini | 250/223 R |

*Primary Examiner*—John K. Corbin
*Assistant Examiner*—Wm. H. Punter
*Attorney, Agent, or Firm*—Spencer & Kaye

[57] ABSTRACT

The device for the testing through optical inspection of the cigarette ends comprises two probes made of optical fibres, which probes are arranged orthogonally with respect to each other. A first probe inspects the end surface of the cigarette being tested by directing against the said end surface a beam of light, and picking up the light reflected, the intensity of which depends from the end surface itself and from the distance of said end surface with respect to the said first probe. A second probe inspects a portion of the side surface of the cigarette comprising also the end being tested, by directing against the side surface a beam of light which provides for an inspection field of which only one part is interested by the cigarette end, and picking up the light reflected by the said side surface, the intensity of which depends from the length of the portion of cigarette end which is covered by the field of inspection and which depends from the actual length of the cigarette or from its axial positioning with respect to the probes. The light reflected by the end surface and the light reflected by the side surface are transformed into electric signals, which are compared in algebraic relationship the one with the other, and the resulting signal is used as a measure for the testing of the cigarette end.

3 Claims, 1 Drawing Figure

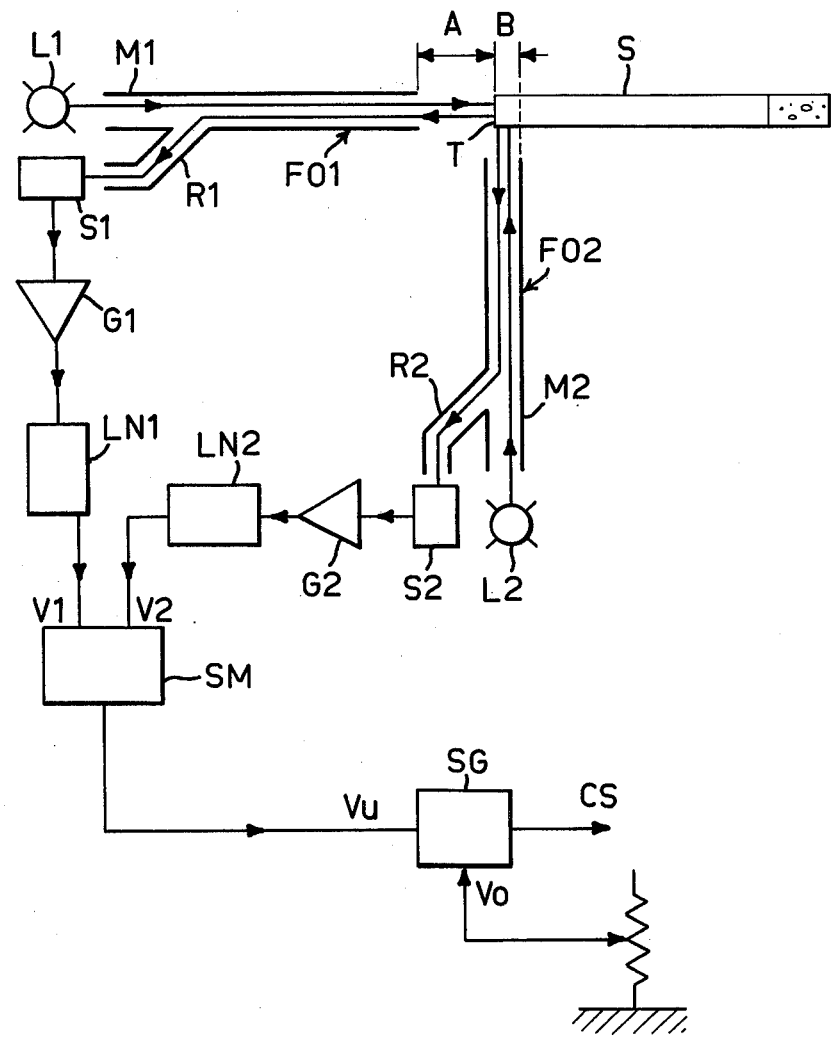

OPTICAL CIGARETTE END INSPECTION DEVICE

SUMMARY OF THE INVENTION

The present invention relates to optical devices for inspecting the end of cigarettes which are delivered by cigarette-making machines in rows of cigarettes lying side by side and moving transversally to the direction of their length.

Particularly, but not exclusively, this invention relates to the inspection of cigarettes provided with a filter tip, and consequently the end inspection involves only the tobacco end.

The cigarette end inspection, in the optical devices, is based on the measurement of the light reflected by the cigarette end, which is illuminated with a constant intensity.

Obviously, this measurement presupposes that the distance between the optical measuring head and the surface of the cigarette end being tested remains constant for all the cigarettes, since a variation of this distance would cause an optical picking error which invalidates the test and consequently the rejection control promoted by said test.

Now, even if the cigarettes to be tested are set with their filter ends perfectly aligned, the opposite ends to be tested may not be equally aligned, because of a certain cigarette cut tolerance range which, if admissible under other points of view, cannot be admitted in such a delicate test as the one effected by optical inspection.

The positive or negative deviations of the actual length of the finished cigarettes from a predetermined rated cigarette length can therefore be of prejudice to the accuracy of the cigarette end inspection.

The object of the invention is to provide an optical cigarette end inspection device which is not affected either by the axial displacement of the cigarettes in a row or by the possible variations of the cigarette length.

Substantially, the invention relates to an optical device which automatically inspects in succession the ends of a cigarette row advancing along a preset path, this device including at least a pair of probes having groups of light-conveying or emitting optical fibres and groups of light-receiving or picking optical fibres, with the fibres of both groups preferably intermingles in each probe, one of said probes being oriented axially against the end surface of the cigarette to be tested, while the other is oriented laterally against the cigarette, perpendicularly to the longitudinal axis of same, and extends along the side of the cigarette so as to partially protrude beyong the cigarette end to be tested, so that the variation of the reflected light, frontally picked up by the first mentioned probe, and which depends from the distance between the probe and the cigarette end, is accompanied by a correlative variation of the reflected light picked up by the side probe, in relation to the actual length of the cigarette, or to an axial displacement of same, said correlative variation being used to discriminate from the component relative to an actual defect of the cigarette end, the component relative to a variation of length of the cigarette as compared to the predetermined rated length.

BRIEF DESCRIPTION OF THE DRAWING

These and other features of the invention and the resulting advantages will be better understood from the following detailed description of a preferred embodiment, diagrammatically illustrated in the attached drawing, in which the electronic part of the electric circuit is illustrated as a block diagram, each block indicating a component which is well known the a person skilled in the art.

DESCRIPTION AND OPERATION OF THE PREFERRED EMBODIMENT

With reference to the drawing, the optical cigarette end inspection device comprises a pair of optical fibre probes FO1 and FO2, both arranged at the side of the end T of the cigarette S to be inspected. The end, or output head, of the probe FO1 faces frontally the end T of the cigarette S. Said probe FO1 presents a circular section the diameter of which depends upon the diameter of the cigarette being tested, and preferably consists of a plurality of intermingled light-emitting and light-receiving fibres.

The other probe FO2 also is made of a plurality of intermingled light-emitting and light-receiving fibres, and its end or output head presents a rectangular section with its greater side arranged parallely to the longitudinal axis of the cigarette, said greater side presenting such a length so that normally the probe end projects for a certain distance beyond the end T of the cigarette S, thus providing a field of inspection of which only one part covers the side of the cigarette end. From the above it is apparent that the two probes FO1 and FO2 are arranged orthogonally with respect to each other.

The bundle M1 of light-emitting fibres of the probe FO1 conveys the light of a lamp L1 presenting a constant intensity of light, in the direction of the cigarette end T, and the bundle R1 of light-receiving fibres of the said probe FO1 picks up the light reflected by the said cigarette end T and conveys same to a photoelectric transducer S1, the output signal of which is applied to the input of amplifier G1, the output of which is applied, in turn, to the input of a linearization circuit LN1. The linearization circuit LN1 thus supplies an output voltage V1 which is proportional to the distance A between the end or head of probe FO1 and the end T of the cigarette S. In this manner, the intensity of the light reflected by the cigarette end surface is converted into the electric signal V1.

In an analogous manner, the light supplied by the lamp L2 (having a constant intensity of light) is conveyed, through the bundle M2 of light-emitting fibres of probe FO2, towards the cigarette side, and a certain amount of said light is reflected by the cigarette paper forming the side of cigarette S, and picked up by the receiving fibres of the bundle R2 of the same probe FO2. This reflected light, the intensity of which is proportional to the length B of the cigarette side which faces the field of inspection of the probe, is transformed into an electric signal V2, by being processed through photoelectric transducer S2, amplifier G2 and linearization circuit LN2. It appears evident that the thus obtained electric signal V2 is proportional to the said length B of cigarette side facing the probe FO2, which length B depends from the actual length of the cigarette S, or its positioning on the conveying device (such as a fluted drum), or both, and which therefore is subject to variations (positive or negative) with respect to the predetermined rated length of the cigarette.

Signals V1 and V2 are applied to the input of an algebraic summing circuit SM, and particularly the signal V2 is utilized, in said summing circuit, to compensate the signal V1 originating from probe FO1, as for what concerns its component relating to the distance A between the head of said probe FO1 and the end T of the cigarette S, the degree of filling of which is to be tested.

As a matter of fact, if the distance between the probe FO1 and the cigarette end T increases, there takes place, in the same measure, a decrease of the length B of the paper side facing the probe FO2. Correspondingly, there takes place a decrease of the intensity of the light reflected by the end T, i.e. a decrease of the electric signal V1, and a decrease of the light reflected by the paper, which corresponds to a decrease of the signal V2.

Therefore it is evident that, under the same conditions of the cigarette ends, that is when the said cigarette ends present a regular degree of filling, the difference between the two signals V1 and V2 remains constant for all cigarettes, independently from their axial positioning with respect to the probe FO1, or from their length (that is to say, independently from the value of the distance A). The difference Vu between the two signals V1 and V2 is compared in a threshold circuit SG with a sample signal Vo.

It is therefore also evident that, for all regular cigarettes, such comparison will result in voltages Vu and Vo of equal value, and no signal will be issued by the output of the threshold circuit SG.

If, on the contrary, a cigarette presents some irregularity at its end T being tested, signal Vu, containing also the information relating to such irregularity, will deviate from the parity comparison with the sample signal Vo, thus causing the emission from the threshold circuit SG of a reject signal CS which will eventually cause the rejection of the defective cigarette.

It is believed that the invention will have been clearly understood from the foregoing detailed description of one preferred embodiment. Changes in the details of construction may be resorted to without departing from the spirit of the invention, and it is accordingly intended that no limitation be implied and that the hereto annexed claims be given the broadest interpretation to which the employed language fairly admits.

I claim:

1. A method for the testing through optical inspection of cigarette ends, comprising the steps of:
   a) axially illuminating the end surface of the cigarette by a first source of light having a constant intensity, and utilizing the light reflected by the said end surface as a measure for the testing;
   b) illuminating a portion of the side surface of the same cigarette end by another source of light perpendicular to said first source of light and having a constant intensity, providing a predetermined field of inspection of which only one part covers said side surface, and utilizing the light reflected by the said side surface to compensate the variations of the said measure for the testing which are consequent to variations in the distance of the cigarette with respect to the said first source of light.

2. A method according to claim 1, in which the light reflected by the cigarette end surface and the light reflected by the portion of the side surface of the cigarette are transformed into electric signals, said electric signals being compared in algebraic relationship the one with the other, so as to generate a resulting signal which is used as a measure for the testing of the cigarette end.

3. A device for the testing through optical inspection of cigarette ends, comprising:
   a. a first fixed probe constructed of optical fibres and directed axially against the end surface of the cigarette to be tested, said first probe serving both for illuminating the said surface end and for picking the reflected light to convey it to a first photoelectric transducer connected to an electric circuit, for the conversion of the light reflected from the end surface of the cigarette into an electric signal presenting a component which corresponds to the distance between the said first probe and the cigarette end;
   b. a second fixed probe constructed of optical fibres and directed perpendicularly to the axis of the said first probe and to the axis of the cigarette, said second probe serving both for illuminating an inspection field of which only one part is provided by a portion of the side surface of the end of the cigarette to be tested, and for receiving the light reflected from the said portion of the side surface of the cigarette to convey it to a second photoelectric transducer connected to an electric circuit for the conversion of the light reflected by the side surface of the cigarette into an electric signal corresponding to the portion of said side surface being illuminated;
   c. means for comparing the said electric signals the one with respect to the other, so as to generate a resulting signal which is used as a measure for the testing of the cigarette end.

* * * * *